United States Patent [19]

Poon

[11] Patent Number: 5,050,593
[45] Date of Patent: Sep. 24, 1991

[54] RESPIRATOR TRIGGERING MECHANISM

[75] Inventor: Chi-Sang Poon, Lexington, Mass.

[73] Assignee: Massachusetts Institute of Technology, Cambridge, Mass.

[21] Appl. No.: 531,949

[22] Filed: Jun. 1, 1990

[51] Int. Cl.$^5$ .............................................. A61M 16/20
[52] U.S. Cl. ............................ 128/204.23; 128/205.24
[58] Field of Search ...................... 128/204.23, 204.26, 128/205.24, 207.14, 204.18; 251/5

[56] References Cited

U.S. PATENT DOCUMENTS

| | | | |
|---|---|---|---|
| 2,814,291 | 11/1957 | Holmes | 128/142 |
| 3,385,295 | 5/1968 | Beasley | 128/145.8 |
| 3,817,246 | 6/1974 | Weigl | 128/145.8 |
| 3,896,800 | 7/1975 | Cibulka | 128/145.8 |
| 3,942,547 | 3/1976 | Pfitzner | 137/102 |
| 3,952,773 | 4/1976 | Hahn | 137/604 |
| 4,176,666 | 12/1979 | Hovey | 128/205.17 |
| 4,256,130 | 3/1981 | Smith et al. | 251/5 |
| 4,421,113 | 12/1983 | Gedeon et al. | 128/204.23 |
| 4,575,042 | 3/1986 | Grimland et al. | 251/46 |
| 4,838,257 | 6/1989 | Hatch | 128/205.24 |

Primary Examiner—Edgar S. Burr
Assistant Examiner—Stephen R. Funk
Attorney, Agent, or Firm—Hamilton, Brook, Smith & Reynolds

[57] ABSTRACT

Mechanism for triggering the inspiratory phase of a respirator having a three-way connector with an inspiratory conduit and an expiratory conduit, each communicating with the respirator and with a patient communicating conduit. Valve mechanism associated with both the expiratory and inspiratory conduits are automatically operated by a patient attempting to breathe, such that he is only exposed to the air volume in the three-way connector and not to the greater air volume of the respirator and its connected tubing.

4 Claims, 3 Drawing Sheets

RESPIRATOR TRIGGERING MECHANISM

FIELD OF THE INVENTION

This invention relates generally to triggering lung ventilating respirators and, more particularly, to a mechanism connecting a patient to a respirator for initiating the respiratory phase of the respirator.

BACKGROUND OF THE INVENTION

Mechanical ventilation of the lungs is a routine life-sustaining therapy in medical intensive care units for patients suffering from respiratory failure. Most respirators in use today for this purpose are of the positive pressure type in which the lungs are inflated by a positive pressure supplied by the respirator during insufflation, followed by passive exhalation as the respirator pressure is removed, whereupon the lungs and chest wall recoil from their inflated positions. In patients who retain some spontaneous breathing activity, lung inflation may also be due in part to the patient's own respiratory efforts. In this instance, the respirator acts as a mechanical assist to the patient, partially reducing the work involved and energy expended while the patient performs the breathing.

In order to maximize the mechanical efficiency of assisted respiration and minimize the patient's risk of exposure to excessive respirator pressure, it is important to synchronize the assisting pressure of the respirator to the patient's breathing efforts. Most modern respirators are equipped with triggering systems that detect the patient's attempt to inhale, and, in response, initiate the insufflation phase. A common design detects any precipitous fall in patient airway pressure at the end of exhalation as a sign of a spontaneous inspiratory effort. As the pressure falls below a threshold level, the respirator is triggered to begin an insufflation phase. To guard against mal-triggering, the pressure threshold cannot be made too sensitive.

For the airway pressure to fall below threshold, the patient must evacuate, by his own active inspiratory efforts, a sizable volume from the respiratory circuit which includes the respirator tubings, connectors, passageway, humidifier and accessories which may be associated with them. In those patients with stiff lungs and small lung capacities (e.g., infants with haline membrane disease), the inspiratory effort required to trigger the respirator may become prohibitive, especially if the evacuation volume in the inspiratory circuit is relatively large compared to the capacity of their lungs. Thus, inspiratory triggering by such patients is often difficult, if at all possible.

Prior attempts in overcoming these problems have included various means of detecting chest wall movement or air flow near the airway opening using plethysmographic methods or flow transducers, respectively. Thus, lung expansion, instead of airway pressure, is used as the triggering signal. These approaches require relatively elaborate instrumentation that is cumbersome, costly, and difficult to operate. Bulky and delicate volume or flow sensors must be attached directly to the patient. None of these methods have been proven effective in allowing sensitive and reliable inspiratory triggering.

Ideally, an inspiratory triggering device should be sensitive enough to provide the desired triggering with minimum encumbrance to the patient, and yet simple enough to be relatively light-weight, flexible, and low-cost. Furthermore, it should not adversely affect the well being of the patient or cause unnecessary inconvenience to the therapist in its operation. Such a device is presently lacking.

On the other hand, an advantage of pressure triggering is that a pressure signal can be readily obtained by way of a side tap to the respiratory circuit proximal to the patient while direct attachment of the pressure transducer to the patient is not necessary. Its disadvantage, however, as used in current practice, is that the airway pressure that provides the trigger can be greatly attenuated in the presence of a large evacuation volume in the respiratory circuit. Apparatus that eliminates or minimizes the effect of the evaluation volume would be useful in providing sensitive pressure triggering and, hence, an object of the present invention.

SUMMARY OF THE INVENTION

The invention resides in triggering mechanism for initiating a inspiratory phase of a respirator and includes a three-way connector which has an inspiratory conduit and an expiratory conduit. Both conduits are in communication with the respirator, as well as with a patient communicating conduit. A one-way valve is associated with the expiratory conduit to permit air (breath) flow only to the respirator and not from it. A shutter valve is associated with the inspiratory conduit to selectively permit air flow from the respirator to the patient. A pressure chamber surrounds and controls the operation of the inspiratory or shutter valve in response to changes in pressure in the expiratory conduit caused by a patient attempting to breathe.

An air tap in the patient communicating conduit is connected to the respirator and when it detects a pressure change in the patient communicating tube of the three-way conduit, it triggers the respirator.

Thus, the one-way valve in the expiratory conduit is a first closure valve and the shutter valve associated with the inspiratory conduit is a second closure valve. Together when closed, they isolate the patient from the air volume associated with the respirator and those tubes communicating with it. He is thus exposed only to the air volume of the three-way connector.

The above and other features of the invention, including various novel details of construction and combinations of parts, will now be more particularly described with reference to the accompanying drawings and pointed out in the claims. It will be understood that the particular respirator triggering mechanism embodying the invention is shown by way of illustration only and not as a limitation of the invention. The principals and features of this invention may be employed in varied and numerous embodiments without departing from the scope of the invention.

BRIEF DESCRIPTION OF THE DRAWINGS

FIG. 4 is an enlarged, sectional detailed view of the expiratory valve in the open position.

FIG. 7 is an enlarged, sectional view of the inspiratory valve in the open position.

DETAILED DESCRIPTION OF THE INVENTION

Figure 1:
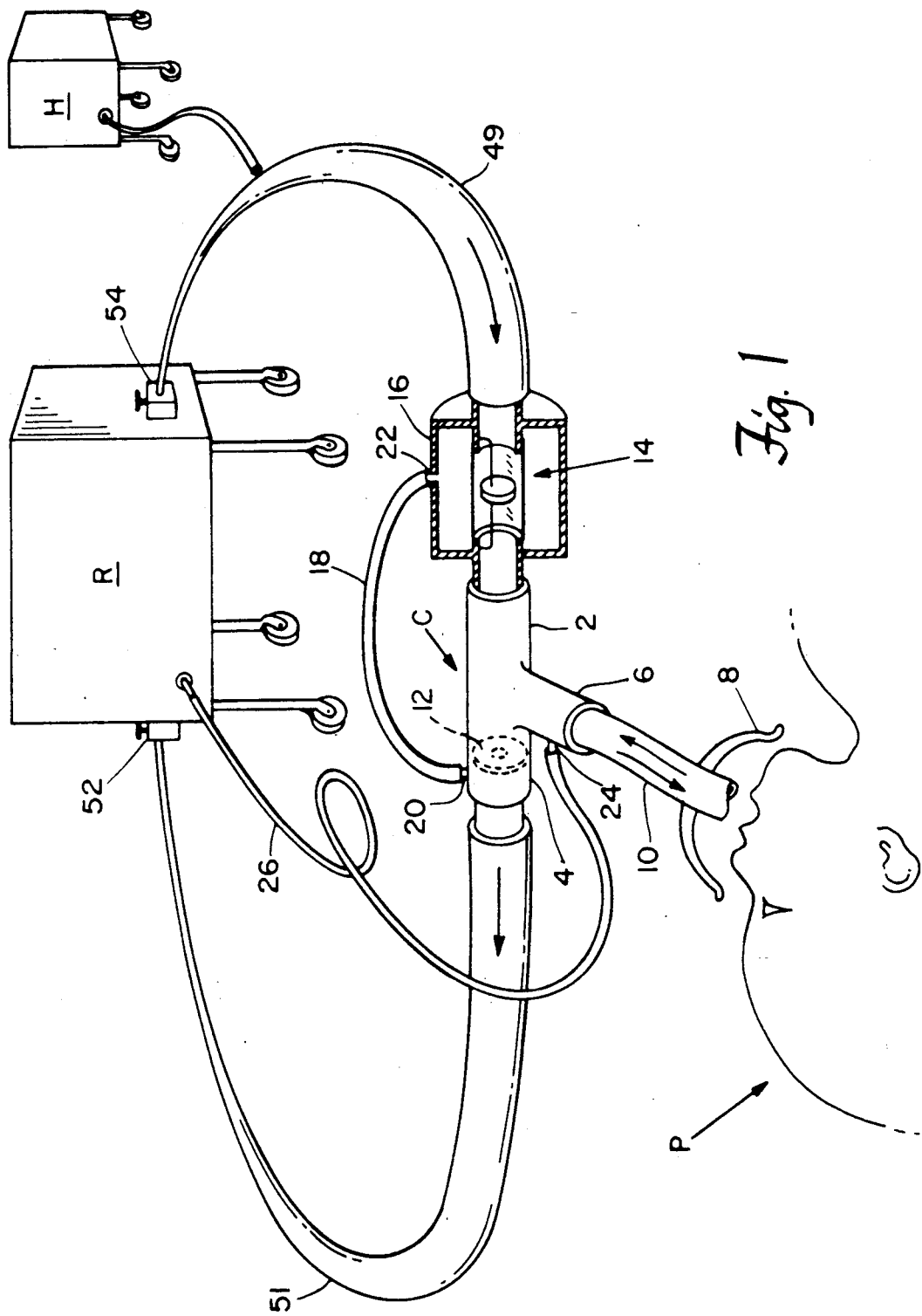
FIG. 1 is a schematic, perspective view, partly in section, of a respirator triggering mechanism embodying the invention and shown connecting a patient to a respirator.

FIG. 1 schematically shows the triggering device embodying the invention connecting a patient P to a respirator R. A three-way connector C, has an inspiratory conduit 2 and expiratory conduit 4, each in communication with a patient connecting conduit 6 and the respirator R. The three-way connector may be made of polystyrene, polypropylene, polycarbonate or any other surgically acceptable material. Wherein a facial mask 8 is shown, a tracheal tube 10 alone could also be employed if conditions dictated.

A one-way closure or expiratory valve 12 is associated with the expiratory conduit 4 to permit air (breath) flow only to the respirator, as shown by an arrow.

Figure 2:
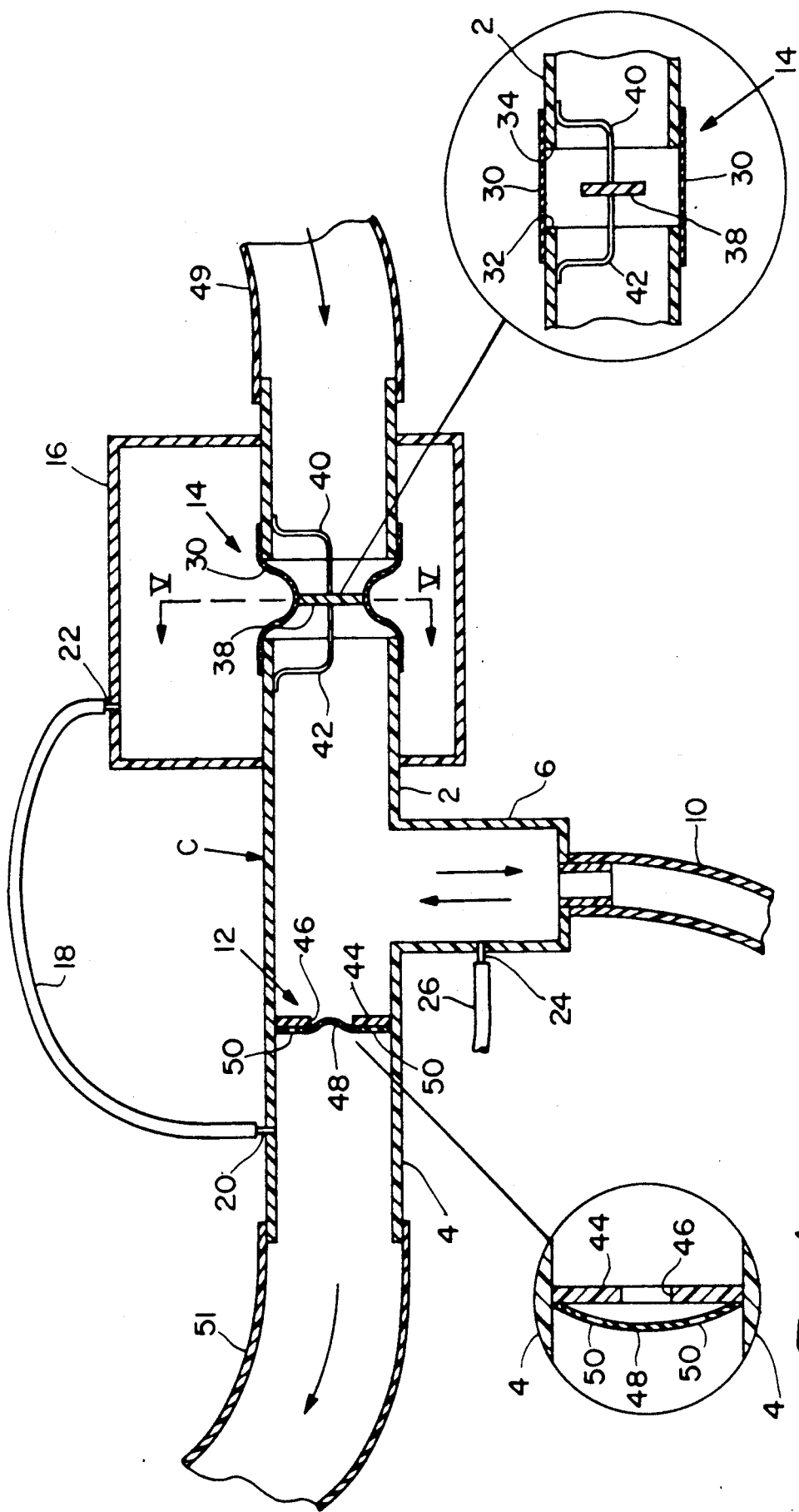
FIG. 2 is a sectional view on an enlarged scale of the device shown at the time of inspiratory occlusion, when both its inspiratory and expiratory valves are in the closed positions.

A shutter or inspiratory valve generally designated 14, is associated with the inspiratory conduit 2 to selectively permit air flow from the respirator R to the patient. A pressure chamber 16 surrounds the inspiratory valve 14 and operates to open and close the valve in response to pressure change in the expiratory conduit 4 by the patient attempting to breathe. The expiratory conduit 4 is in communication with the pressure chamber 16 via a tube 18 connecting a tap 20 in the conduit to a tap 22 in the chamber. A side tap 24, which may also be called a pressure tap or air tap, in the patient conduit 6, is, as seen in FIGS. 1 and 2, a hollow tube in an opening in the patient conduit 6 which is connected to the respirator R by a flexible tube 26, allows the detection of airway pressure of the patient. The side tap 24 may be located any place in the three-way connector C within the confines of the valves 12 and 14.

The inspiratory or shutter valve assembly 14 situated in the inspiratory conduit 4 of the three-way connector is as close as possible to the junction of the conduit to make the volume of the connector C as small as possible. The valve assembly 14 comprises a collapsible elastomeric ring 30 made, for example, of latex, is expanded and placed over two otherwise open ends 32, 34 (FIG. 7) of the inspiratory conduit 2. A concentric shutter disc 38 is located in the lumen of the inspiratory conduit 2 and is held in place by stems 40, 42 affixed to the inner wall of the conduit 4. The exterior of the flexible tube 30 is surrounded by the airtight pressure chamber 16 which, in turn, communicates with the expiratory conduit 4 via the tube 18.

Figure 3:
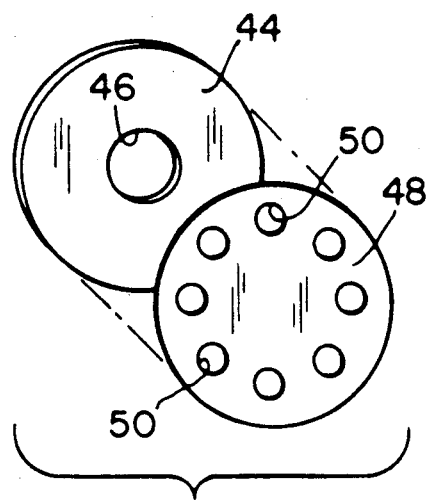
FIG. 3 is an enlarged, perspective, detailed view of the one-way or expiratory valve of the device.

As seen in FIGS. 3 and 4, the expiratory valve 12 has an annular plastic disc 44 secured to the inner walls of the conduit 4. It has a control opening 46. A membrane, or perforated diaphragm, 48 (also made, for example, of latex) has a plurality of circularly located openings 50. It is secured only at its periphery to the disc 44. There are no perforations in the center of the membrane which overlies the aperture 46 in the disc 44.

When air pressure on the right of the valve 12 is greater than on the left, as viewed in FIG. 2, air moves through the central aperture 46 of the disc 44, causing the membrane 48 to bulge outwardly to the left, as seen in FIG. 4, whereupon the air then exits through the apertures 50 in the membrane. When the pressure is reversed, air does not flow. In this instance, the pressure differential causes the membrane 48 to close the central aperture 46 with the membrane openings 50 located against the non-aperture portion of the disc 44 preventing flow from left to right, as viewed in FIGS. 2 and 4. The valve 12 is merely illustrative of one-way valves. Any equivalent valve may be employed.

Figure 5:
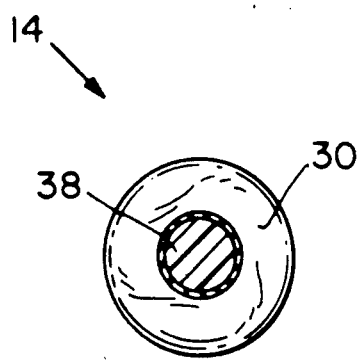
FIG. 5 is a detailed view of the shutter or inspiratory valve taken on the line V—V on FIG. 1.
Figure 6:
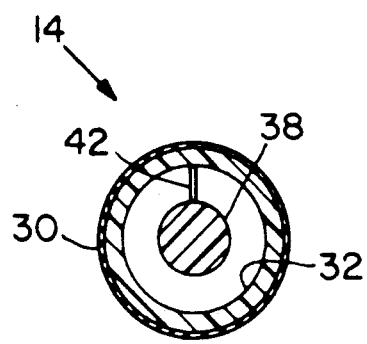
FIG. 6 is a detailed view of the inspiratory valve also taken on the line V—V but with the valve in the open position.

FIGS. 6 and 7 show the inspiratory valve 14 in the open position with the flexible, elastomeric tube 36 out of engagement with the shutter disc 38, whereby air may flow from right to left from the respirator R via a tube 49. FIGS. 2 and 5 show the inspiratory valve 14 in closed position which takes place when the pressure in the chamber 16 is greater than the pressure in the inspiratory conduit 4. At this time, the flexible, collapsible, elastomeric tube 30 closes down and seals against the central shutter disc 38. If desired, this disc 38 may be eliminated. In this instance, the tube 30 will collapse upon itself.

The triggering device operates in the following manner: during the expiratory phase of the patient's breathing cycle, the expiratory valve 52 of the respirator R (FIG. 1) is open while the corresponding inspiratory valve 54 is closed. This results in no air flowing from the respirator R to the patient P via the tube 49. However, the tube 51 is then open to the respirator. The patient exhales through the face mask 18 (or the tracheal tube 10), the conduit 6 and thence through the aperature 46 of the annular one-way valve 12 and then through the perforations 50 of the elastomeric membrane 48. Throughout the patient's expiratory phase, his airway pressure approximately equals the pressure in the expiratory conduit 4 and, thus, the pressure chamber 16 of the T-shaped, three-way valve. At the end of patient expiration and the beginning of inspiration, his airway pressure begins to fall while the pressure in the conduit 6 and, hence, in the pressure chamber 16 remains steady at the end-expiratory level.

The resulting pressure gradient causes the elastomeric membrane 48 of the one-way valve 12 to seal against the annular ring 44, as seen in FIG. 2. This prevents retrograde gas flow from the expiratory tubing 51 and conduit 4 back to the patient. The relatively large gas volume in the expiratory tubing 4 to the left or downstream side of the one way valve 12 and the large connection tube 51 is, therefore, separated from the patient. Since the pressure in the chamber 16 is greater than the pressure in the inspiratory conduit 2, the shutter or inspiratory vale 14 is closed, as seen in FIG. 2.

In the case of an adult patient with stronger lungs than a premature infant, it may not be necessary to employ the chamber 16. The decreased pressure in the connector C being less than ambient will cause the tube 30 to collapse.

Thus, it will be seen, with both the one-way valve 12 and the shutter or inspiratory valve 14 both closed, the patient is then shielded or isolated from the large gas volume in the expiratory conduit 4 and 51 and the inspiratory conduit 2 and the tubing 49, as well as the volume of any accessory equipment, such as a humidifier H, connected to these tubes.

The pressure of the pressure chamber 16 insures that the exterior of the elastomeric tubing 30 is referred to any positive end expiratory pressure level in the preceding breath. Because of the simultaneous occlusion of both the inspiratory and expiratory valves 14 and 12, respectively, gas evacuation, due to inspiratory suction by the patient is confined to the relatively small volume inside the three-way connector, as then limited by those valves and the patient's lung. The patient is only exposed to the relatively small volume in the three-way connector C. This allows the patient's airway pressure to fall more rapidly than ordinarily possible if he were acting against a large volume. Thus, the patient, particularly those with small lungs or with weak lungs, needs only to inhale against a very small volume.

The change in patient airway pressure is detected by a pressure transducer of the respirator (not shown) which is connected by way of plastic tubing 26 to the side tap 24 in the patient conduit 6. As the patient airway pressure falls below a preset threshold value relative to the end expiratory pressure, the respirator R is triggered to begin the insufflation phase. Since the pressure transients in the inspiratory and expiratory tubings are eliminated, the pressure threshold can be set at a much more sensitive level without causing maltriggering.

Once the respirator R is triggered, the expiratory valve 52 of the respirator R is then closed and the inspiratory valve 54 of the respirator R is then opened. The ensuing positive insufflation pressure from the respirator distends the elastomeric sleeve 30 returning the valve 14 to its normally open position and delivering inspiratory gas to the patient.

We claim:

1. A system for triggering insufflation by a respirator comprising:
   a) a connector, including,
      i) an inspiratory conduit for connection to an inspiratory valve of the respirator,
      ii) an expiratory conduit for connection to an expiratory valve of the respirator, and
      iii) a patient-connecting conduit for connection with a breathing passage of a patient;
   b) a one-way expiratory valve disposed in the expiratory conduit which is moveable from a closed position to an open position responsive to exhalation of the patient through the patient-connecting conduit, whereby the patient's breath passes through the one-way expiratory valve to the respirator when the respirator is in an expiratory mode;
   c) a shutter valve disposed in the inspiratory conduit, said shutter valve including a collapsible elastomeric ring and being moveable between an open position, wherein fluid communication is provided between the patient-connecting conduit and the inspiratory valve through the elastomeric ring, and a closed position by collapse of the collapsible elastomeric ring, whereby the shutter valve seals the patient-connecting conduit from the inspiratory valve; and
   d) an air tap disposed at a portion of the connector which is between the one-way expiratory valve and the shutter valve and which extends from the connector to the respirator, and responsive to voluntary inhalation by the patient to move the one-way expiratory valve and the shutter valve from their open positions to their closed positions to cause pressure within the connector and in the air tap to diminish in an amount sufficient to trigger the respirator to shift from an expiratory mode to an inspiratory mode, in which the expiratory valve closes and the inspiratory valve opens, and in which air is directed from the respirator through the inspiratory valve to force the shutter valve from the closed position to the open position, thereby causing insufflation of the patient by the respirator.

2. A system of claim 1, wherein the shutter valve further includes a shutter disc disposed within the elastomeric ring and means for supporting the shutter disc within the elastomeric ring, whereby the shutter disc and the collapsible elastomeric ring define an annulus which provides fluid communication between the patient-connecting conduit and the inspiratory valve when the shutter valve is in the open position, thereby allowing collapse of the collapsible elastomeric ring about the shutter disc when the shutter valve closes to seal the patient-connecting conduit from the inspiratory valve.

3. A system of claim 2 further including:
   a) a pressure housing disposed about the collapsible elastomeric ring; and
   b) a tube extending between the pressure housing and a portion of the expiratory conduit which is disposed between the one-way expiratory valve and the expiratory valve, whereby fluid communication is provided between the pressure housing and the expiratory conduit, thereby causing the pressure within the pressure housing to be substantially equal to pressure within the portion of the expiratory conduit between the one-way expiratory valve and the expiratory valve.

4. A system of claim 3 wherein the one-way expiratory valve includes a perforated diaphragm engageable with an apertured disc.

* * * * *